US008399507B2

(12) United States Patent
Liang et al.

(10) Patent No.: US 8,399,507 B2
(45) Date of Patent: Mar. 19, 2013

(54) ANTIDIABETIC TRICYCLIC COMPOUNDS

(75) Inventors: Gui-Bai Liang, Scotch Plains, NJ (US);
Xibin Liao, Edison, NJ (US); Weiguo Liu, Princeton, NJ (US); Paul E. Finke, Milltown, NJ (US); Dooseop Kim, Westfield, NJ (US); Lihu Yang, Edison, NJ (US); Songnian Lin, Monroe, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 324 days.

(21) Appl. No.: 12/738,857

(22) PCT Filed: Oct. 27, 2008

(86) PCT No.: PCT/US2008/012181
§ 371 (c)(1),
(2), (4) Date: Apr. 20, 2010

(87) PCT Pub. No.: WO2009/058237
PCT Pub. Date: May 7, 2009

(65) Prior Publication Data
US 2010/0216694 A1   Aug. 26, 2010

Related U.S. Application Data

(60) Provisional application No. 61/000,857, filed on Oct. 29, 2007.

(51) Int. Cl.
*A61K 31/38* (2006.01)
*A61K 31/34* (2006.01)
*C07D 305/00* (2006.01)
*C07C 62/00* (2006.01)

(52) U.S. Cl. ........ 514/443; 514/468; 514/411; 514/469; 514/597; 549/510; 562/452; 562/466; 562/506; 562/508; 562/510

(58) Field of Classification Search ................... 549/510; 514/443, 468, 411, 569, 567; 562/452, 466, 562/506, 508, 510
See application file for complete search history.

(56) References Cited

U.S. PATENT DOCUMENTS

| 7,119,198 | B2 | 10/2006 | Lohray et al. | |
| 7,442,808 | B2* | 10/2008 | Ge et al. | 549/44 |
| 7,517,992 | B2* | 4/2009 | Antonov et al. | 546/256 |
| 7,820,837 | B2* | 10/2010 | Yasuma et al. | 549/407 |
| 2006/0167055 | A1 | 7/2006 | Antonov et al. | |
| 2006/0258722 | A1 | 11/2006 | Yasuma et al. | |
| 2007/0265332 | A1 | 11/2007 | Ge et al. | |

FOREIGN PATENT DOCUMENTS

| WO | 2007/013689 | 2/2007 |
| WO | 2007/106469 | 9/2007 |

OTHER PUBLICATIONS

International Search Report for U.S. Appl. No. 12/738,857.
Supplemental European Search Report of EP 08846153, dated Mar. 16, 2011.

* cited by examiner

*Primary Examiner* — Andrew D Kosar
*Assistant Examiner* — Raymond Covington
(74) *Attorney, Agent, or Firm* — Anna L. Cocuzzo; Kenrick L. Vidale; John C. Todaro

(57) ABSTRACT

Tricyclic compounds containing a cyclopropanecarboxylic acid fused to a bicyclic ring, including pharmaceutically acceptable salts, are agonists of G-protein coupled receptor 40 (GPR40) and are useful as therapeutic compounds, particularly in the treatment of Type 2 diabetes, and of conditions that are often associated with this disease, including obesity and lipid disorders, such as mixed or diabetic dyslipidemia, hyperlipidemia, hypercholesterolemia, and hypertriglyceridemia.

4 Claims, No Drawings

ANTIDIABETIC TRICYCLIC COMPOUNDS

CROSS REFERENCE TO RELATED APPLICATIONS

This application is the National Stage of International Application No. PCT/US2008/012181, filed 27 Oct. 2008, which claims the benefit under 35 U.S.C. 119(e) of U.S. Provisional Application No. 61/000,857, filed 29 Oct. 2007.

FIELD OF THE INVENTION

The instant invention relates to novel tricyclic compounds containing a cyclopropanecarboxylic acid fused to a substituted indane nucleus, including pharmaceutically acceptable salts thereof, which are agonists of G-protein-coupled receptor 40 (GPR40) and are useful as therapeutic compounds, particularly in the treatment of Type 2 diabetes mellitus, and of conditions that are often associated with this disease, including obesity and lipid disorders.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body. Patients having Type 2 diabetes have a resistance to the effects of insulin in stimulating glucose and lipid metabolism in the main insulin-sensitive tissues, which are muscle, liver and adipose tissues. These patients often have normal levels of insulin, and may have hyperinsulinemia (elevated plasma insulin levels), as they compensate for the reduced effectiveness of insulin by secreting increased amounts of insulin. Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the Metabolic Syndrome. According to one widely used definition, a patient having Metabolic Syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether or not they have or develop overt diabetes mellitus, have an increased risk of developing the macrovascular and microvascular complications that occur with Type 2 diabetes, such as atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is very poor because of well-entrenched sedentary lifestyles and excess food consumption, especially of foods containing high amounts of fat and carbohydrates. Pharmacologic treatments have focused on three areas of pathophysiology: (1) hepatic glucose production (with biguanides, such as metformin), (2) insulin resistance (with PPARγ agonists, such as pioglitazone and rosiglitazone), and (3) insulin secretion (with sulfonylureas).

The biguanides are a class of drugs that are widely used to treat Type 2 diabetes. The two best known biguanides, phenformin and metformin, cause some correction of hyperglycemia. The biguanides act primarily by inhibiting hepatic glucose production, and they also are believed to modestly improve insulin sensitivity. The biguanides can be used as monotherapy or in combination with other anti-diabetic drugs, such as insulin or an insulin secretagogue, without increasing the risk of hypoglycemia. However, phenformin and metformin can induce lactic acidosis and nausea/diarrhea. Metformin has a lower risk of side effects than phenformin and is widely prescribed for the treatment of Type 2 diabetes.

The glitazones (i.e. 5-benzylthiazolidine-2,4-diones) are a newer class of compounds that can ameliorate hyperglycemia and other symptoms of Type 2 diabetes. The glitazones that are currently marketed (rosiglitazone and pioglitazone) are agonists of the peroxisome proliferator activated receptor (PPAR) gamma subtype. The PPAR-gamma agonists substantially increase insulin sensitivity in muscle, liver and adipose tissue in several animal models of Type 2 diabetes, resulting in partial or complete correction of elevated plasma glucose levels without the occurrence of hypoglycemia. PPAR-gamma agonism is believed to be responsible for the improved insulin sensititization that is observed in human patients who are treated with the glitazones. New PPAR agonists are currently being developed. Many of the newer PPAR compounds are agonists of one or more of the PPAR alpha, gamma and delta subtypes. Compounds that are agonists of both the PPAR alpha and PPAR gamma subtypes (PPAR alpha/gamma dual agonists) have been made and tested, but so far none have been approved by the regulatory authorities. The currently marketed PPAR gamma agonists are modestly effective in reducing plasma glucose and HemoglobinA1C. The currently marketed compounds do not greatly improve lipid metabolism and may actually have a negative effect on the lipid profile. Selective PPAR Gamma Partial Agonists (SPPARM's) are currently being developed and may be equally effective, with fewer side effects, such as weight gain and edema. Thus, the PPAR compounds represent an important advance in diabetic therapy.

Another widely used drug treatment involves the administration of insulin secretagogues, such as the sulfonylureas (e.g. tolbutamide, glipizide, and glimepiride). These drugs increase the plasma level of insulin by stimulating the pancreatic β-cells to secrete more insulin. Insulin secretion in the pancreatic β-cell is under strict regulation by glucose and an array of metabolic, neural and hormonal signals. Glucose stimulates insulin production and secretion through its metabolism to generate ATP and other signaling molecules, whereas other extracellular signals act as potentiators or inhibitors of insulin secretion through GPCR's present on the plasma membrane. Sulfonylureas and related insulin secretagogues act by blocking the ATP-dependent K+ channel in β-cells, which causes depolarization of the cell and the opening of the voltage-dependent Ca2+ channels with stimulation of insulin release. This mechanism is non-glucose dependent, and hence insulin secretion can occur regardless of the ambient glucose levels. This can cause insulin secretion even if the glucose level is low, resulting in hypoglycemia, which can be fatal in severe cases. The administration of insulin secretagogues must therefore be carefully controlled. The insulin secretagogues are often used as a first-line drug treatment for Type 2 diabetes.

Dipeptidyl peptidase IV (DPP-4) inhibitors (e.g., sitagliptin, vildagliptin, alogliptin, denagliptin, and saxagliptin) provide a new route for increasing insulin secretion in response to food consumption. DPP-4 is a cell surface protein with broad tissue distribution that has been implicated in a wide range of biological functions. DPP-4 is identical to the T-cell activation marker CD26 and can cleave a number of immunoregulatory, endocrine, and neurological peptides in vitro. It is well established that the incretins GLP-1 (glucagon-like peptide-1) and GIP (glucose-dependent insulinotropic peptide; also known as gastric inhibitory peptide) stimulate insulin secretion and are rapidly inactivated in vivo by DPP-4. These peptidyl hormones are secreted by endocrine cells that are located in the epithelium of the small intestine. When these endocrine cells sense an increase in the concentration of glucose in the lumen of the digestive tract, they act as the trigger for incretin release. Incretins are carried through the circulation to beta cells in the pancreas and cause the beta cells to secrete more insulin in anticipation of an increase of blood glucose resulting from the digesting meal. Studies with DPP-4(−/−)-deficient mice and clinical trials with DPP-4 inhibitors indicate that DPP-4 inhibition increases the steady state concentrations of GLP-1 and GIP, resulting in improved glucose tolerance. Inactivation of these peptides by DPP-4 may also play a role in glucose homeostasis. DPP-4 inhibitors therefore have utility in the treatment of Type 2 diabetes and in the treatment and prevention of the numerous conditions that often accompany Type 2 diabetes, including Metabolic Syndrome, reactive hypoglycemia, and diabetic dyslipidemia. GLP-1 has other effects that help to lower blood glucose and contribute to glucose homeostasis. GLP-1 inhibits glucagon secretion from the liver. Glucagon is a hormone that increases blood glucose levels by stimulating glucose production from glycogen stores in the liver. GLP-1 also delays stomach emptying, which helps to spread glucose absorption out over time, and thus limit hyperglycemia. Also, studies in animals have shown that GLP-1 can increase the number of beta cells, either through promoting growth or by inhibiting apoptosis. Thus, potentiation of GLP-1 action by preventing its degradation offers several mechanisms to attenuate hyperglycemia associated with Type 2 diabetes.

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have recently been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., Nature, 422: 173 (2003); Briscoe, C. P. et al., J. Biol. Chem., 278: 11303 (2003); Kotarsky, K. et al., Biochem. Biophys. Res. Comm., 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion. There are several potential advantages of GPR40 as a potential target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be highly advantageous, because long term diabetes therapy often leads to the gradual diminution of islet activity, so that after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

SUMMARY OF THE INVENTION

The present invention is directed to novel substituted fused cyclopropanecarboxylic acids, and pharmaceutically acceptable salts thereof, including individual diastereoisomers and enantiomers thereof, and mixtures of diastereoisomers and/or enantiomers thereof, which are agonists of the GPR40 receptor and which are useful in the treatment of diseases that are modulated by GPR40 agonists, including Type 2 diabetes, hyperglycemia that is associated with Type 2 diabetes, insulin resistance, and obesity.

DETAILED DESCRIPTION OF THE INVENTION

The present invention relates to novel substituted fused cyclopropanecarboxylic acids that are useful as agonists of the GPR40 receptor having the following structural formulae:

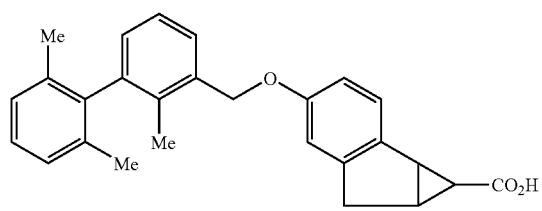
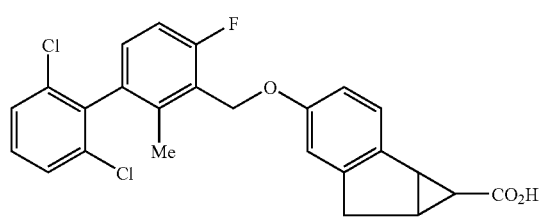
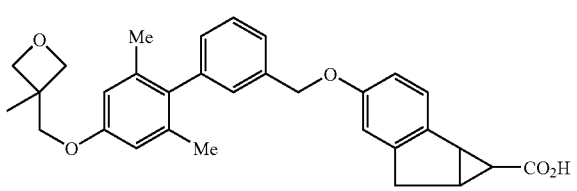
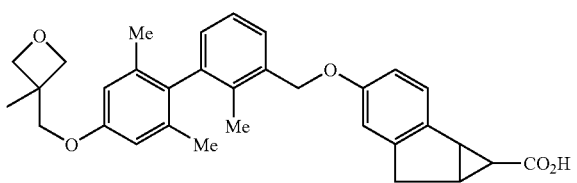
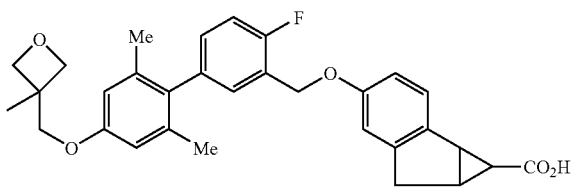
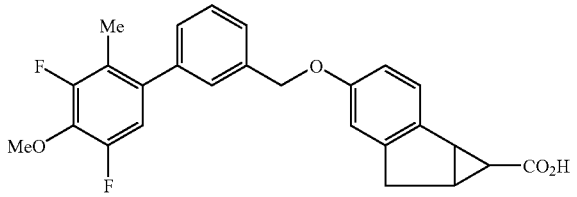
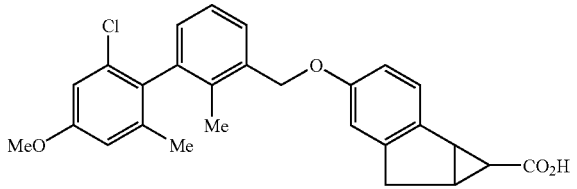
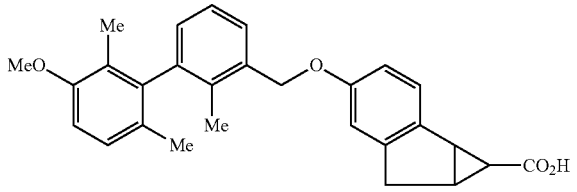

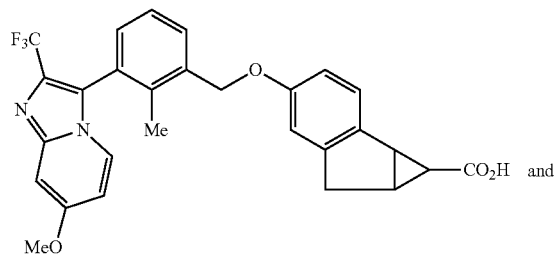
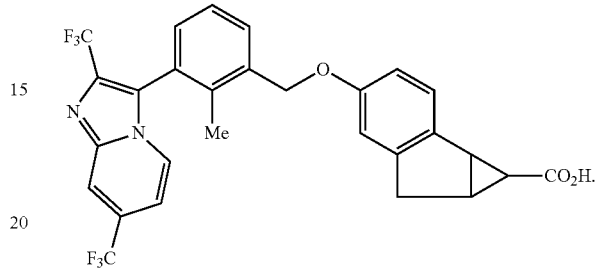

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures. In one embodiment of the present invention, the compounds have the absolute stereochemistry at the three stereogenic carbon centers as indicated below:

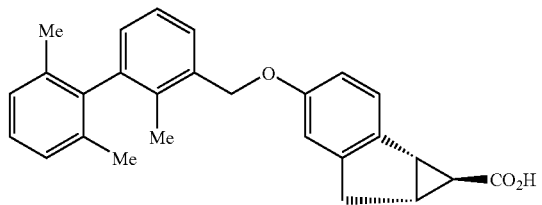
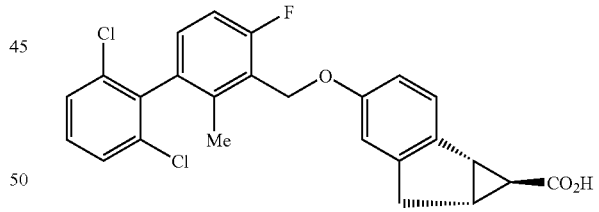
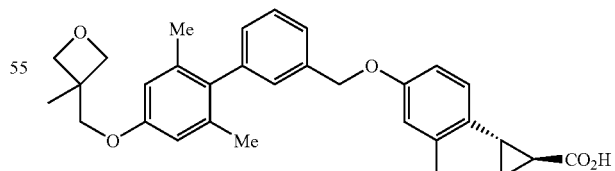
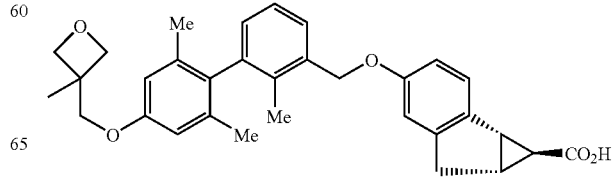

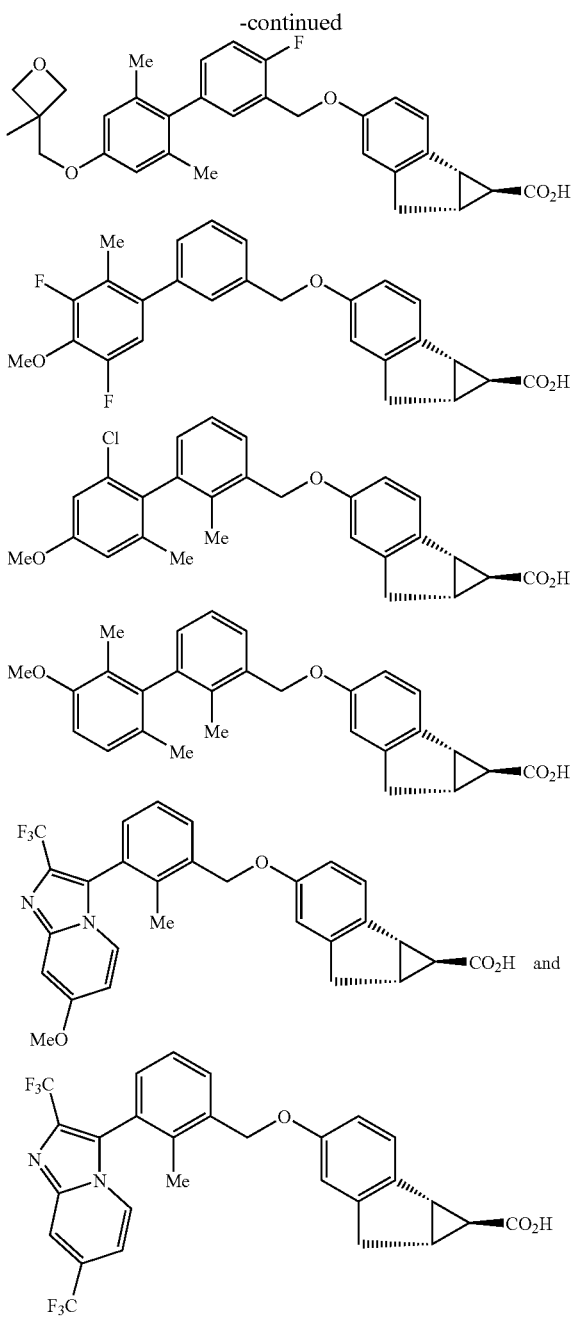

and pharmaceutically acceptable salts thereof.

The invention also includes pharmaceutically acceptable salts of the compounds, and pharmaceutical compositions comprising the compounds and a pharmaceutically acceptable carrier. The compounds are especially useful in treating insulin resistance, Type 2 diabetes, hyperglycemia, and dyslipidemia that is associated with Type 2 diabetes and insulin resistance. The compounds are also useful for the treatment of obesity Although the specific stereochemistries described above are preferred, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a patient in need of treatment. Other medical uses of the compounds of the present invention are described hereinafter.

DEFINITIONS

As used herein the following definitions are applicable.

"Ac" is acetyl, which is $CH_3C(=O)-$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like.

"Cycloalkyl" means a saturated carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. Cycloalkenyl rings comprise a double bond in the ring.

"Aryl" is commonly used to refer to carbocyclic aromatic structures. The most common aryl groups are phenyl and naphthyl. Phenyl is generally the most preferred aryl group.

"Heterocycle" means a saturated or partly unsaturated ring or ring system containing at least one heteroatom selected from N, S and O, wherein the number of heteroatoms and the ring size and the degree of unsaturation (if any) are defined herein. Examples of heterocycles include tetrahydrofuran, piperazine, piperidine, morpholine, oxetane (4-membered cyclic ether), and tetrahydropyran (6-membered cyclic ether).

"Heteroaryl" means a heteroaromatic ring containing at least one ring heteroatom selected from N, O and S (including $SO$ and $SO_2$), as defined more specifically herein. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, quinazolinyl, dibenzofuranyl, and the like.

"Halogen" includes fluorine, chlorine, bromine and iodine.

"Me" represents methyl.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Optical Isomers—Diastereoisomers—Geometric Isomers—Tautomers:

Compounds of the present invention may contain one or more asymmetric centers and can thus occur as racemates, racemic mixtures, single enantiomers, individual diastereoisomers, and mixtures of diastereoisomers and/or enantiomers. The invention is meant to comprehend all such isomeric forms of the compounds of the present invention. Specifically, the compounds of the instant invention have at least three asymmetric centers. Additional asymmetric centers may be present depending upon the nature of the various substituents on the molecule. It is intended that all of the possible optical isomers, stereoisomers, and diastereoisomers in mixtures and as pure or partially purified compounds are included within the scope of this invention (i.e. all possible combinations of the asymmetric centers as pure compounds or in mixtures).

Some of the compounds described herein may contain olefinic double bonds, and unless specified otherwise, are meant to include both E and Z geometric isomers.

Some of the compounds described herein may exist with different points of attachment of hydrogen, referred to as tautomers. An example is a ketone and its enol form, known as keto-enol tautomers. The individual tautomers as well as mixtures thereof are encompassed with compounds of the present invention.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Salts:

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds described herein are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of the following diseases may be treated by the administration of a therapeutically effective amount of a compound of the present invention, or a pharmaceutically acceptable salt thereof, to a patient in need of treatment. Also, the compounds of the present invention may be used for the manufacture of a medicament for treating one or more of these diseases:

(1) non-insulin dependent diabetes mellitus (Type 2 diabetes);
(2) hyperglycemia;
(3) insulin resistance;
(4) the Metabolic Syndrome;
(5) obesity;
(6) hypercholesterolemia;
(7) hypertriglyceridemia (elevated levels of triglyceride-rich-lipoproteins);
(8) mixed or diabetic dyslipidemia;
(9) low HDL cholesterol;
(10) high LDL cholesterol;
(11) hyperapoBliproteinemia; and
(12) atherosclerosis.

Preferred uses of the compounds are for the treatment of one or more of the following diseases by administering a therapeutically effective amount to a patient in need of treatment. The compounds may be used for manufacturing a medicament for the treatment of one or more of these diseases:

(1) Type 2 diabetes, and specifically hyperglycemia associated with Type 2 diabetes;
(2) Metabolic Syndrome;
(3) obesity; and
(4) hypercholesterolemia.

The compounds are expected to be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds of this invention may also have utility in improving or restoring β-cell function, so that they may be useful in treating Type 1 diabetes or in delaying or preventing a patient with Type 2 diabetes from needing insulin therapy.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Pharmaceutical Compositions:

Another aspect of the present invention provides pharmaceutical compositions which comprise a compound of the present invention and a pharmaceutically acceptable carrier. The pharmaceutical compositions of the present invention comprise a compound of the present invention or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

Because of their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may be varied and may conveniently be between about 2 percent to about 60 percent of the weight of the unit. The amount of active compound in such therapeutically useful compositions is such that an effective dosage will be obtained.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil, a solvent, and/or one or more surfactants to enhance solubility.

Combination Therapy:

Compounds of the present invention may be used in combination with other drugs that may also be useful in the treatment or amelioration of the diseases or conditions for which compounds of the present invention are useful. Such other drugs may be administered, by a route and in an amount commonly used therefor, contemporaneously or sequentially with a compound of the present invention. In the treatment of patients who have Type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPARγ agonists, when the patient's glycemic levels are not adequately responding to treatment.

When a compound of the present invention is used contemporaneously with one or more other drugs, a pharmaceutical composition in unit dosage form containing such other drugs and the compound of the present invention is preferred. However, the combination therapy also includes therapies in which the compound of the present invention and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the present invention.

Examples of other active ingredients that may be administered in combination with a compound of the present invention, and either administered separately or in the same pharmaceutical composition, include, but are not limited to:

(a) other dipeptidyl peptidase IV (DPP-4) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as muraglitazar, naveglitazar, tesaglitazar, and TAK-559; PPARα agonists, such as fenofibric acid derivatives (gemfibrozil, clofibrate, fenofibrate and bezafibrate); and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 97/16442; WO 98/04528, WO 98/21957; WO 98/22108; WO 98/22109; WO 99/01423, WO 00/39088, and WO 00/69810; WO 2004/050039; and WO 2004/069158;

(g) GLP-1, GLP-1 analogues or mimetics, and GLP-1 receptor agonists, such as exendin-4 (exenatide), liraglutide (NN-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, bombesin receptor agonists (such as bombesin receptor subtype-3 agonists), cholecystokinin 1 (CCK-1) receptor agonists, and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of cholesteryl ester transfer protein (CETP), such as torcetrapib; and (s) inhibitors of fructose 1,6-bisphosphatase, such as those disclosed in U.S. Pat. Nos. 6,054,587; 6,110,903; 6,284,748; 6,399,782; and 6,489,476.

Dipeptidyl peptidase-IV inhibitors that can be combined with compounds of structural formula I include those disclosed in U.S. Pat. No. 6,699,871; WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); WO 03/000181 (3 Jan. 2003); WO 04/007468 (22 Jan. 2004); WO 04/032836 (24 Apr. 2004); WO 04/037169 (6 May 2004); and WO 04/043940 (27 May 2004). Specific DPP-4 inhibitor compounds include isoleucine thiazolidide (P32/98); NVP-DPP-728; vildagliptin (LAF 237); P93/01; and saxagliptin (BMS 477118).

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," Expert Opin. Ther. Patents, 11: 1677-1692 (2001); D. Spanswick and K. Lee, "Emerging antiobesity drugs," Expert Opin. Emerging Drugs, 8: 217-237 (2003); and J. A. Fernandez-Lopez, et al., "Pharmacological Approaches for the Treatment of Obesity," Drugs, 62: 915-944 (2002).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; U.S. Pat. No. 5,292,736; PCT Publication WO 05/000809; PCT Publication WO 03/086288; PCT Publication WO 03/087037; PCT Publication WO 04/048317; PCT Publication WO 03/007887; PCT Publication WO 03/06378.1; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Melanocortin-4 receptor (MC4R) agonists useful in the present invention include, but are not limited to, those disclosed in U.S. Pat. No. 6,294,534, U.S. Pat. Nos. 6,350,760, 6,376,509, 6,410,548, 6,458,790, U.S. Pat. No. 6,472,398, U.S. Pat. No. 5,837,521, U.S. Pat. No. 6,699,873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187932, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02/092566, WO 03/093234, WO 03/095474, and WO 03/104761.

The potential utility of safe and effective activators of glucokinase (GKAs) for the treatment of diabetes is discussed in J. Grimsby et al., "Allosteric Activators of Glucokinase: Potential Role in Diabetes Therapy," Science, 301: 370-373 (2003).

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-obesity compounds, and anti-hypertensive agents.

BIOLOGICAL ASSAYS

Generation of GPR40-Expressing Cells:

Human and mouse GPR40 stable cell-lines were generated in CHO cells stably expressing NFAT BLA (Beta-lactamase). A human GPR40 stable cell-line was generated in HEK cells stably expressing the aequorin expressing reporter. The expression plasmids were transfected using lipofectamine (Life Technologies) following manufacturer's instructions. Stable cell-lines were generated following drug selection.

FLIPR Assays:

FLIPR (Fluorimetric Imaging Plate Reader, Molecular Devices) assays were performed to measure agonist-induced calcium mobilization of the stable clones. For the FLIPR assay, one day before assay, GPR40/CHO NFAT BLA cells were seeded into black-wall-clear-bottom 384-well plates (Costar) at 1.4×10e4 cells/20 µL medium/well. The cells were incubated with 20 µl/well of the assay buffer (HBSS, 0.1% BSA, 20 mM HEPES, 2.5 mM probenecid, pH 7.4) containing 8 µM fluo-4, AM, 0.08% pluronic acid at room temperature for 100 minutes. Fluorescence output was measured using FLIPR. Compounds were dissolved in DMSO and diluted to desired concentrations with assay buffer. 13.3 µL/well of compound solution was added.

The compounds in these examples all have $EC_{50}$ values less than 100 nanomolar (nM) in the functional assay described above.

Inositol Phosphate Turnover Assay:

The assay is performed in 96-well format. HEK cells stably expressing human GPR40 are plated to be 60-80% confluent within 72 h. After 72 h, the plates are aspirated and the cells washed with inositol-free DMEM (ICN). The wash media is replaced with 150 µL of 3H-inositol labeling media (inositol-free media containing 0.4% human albumin or 0.4% mouse albumin, 1× pen/strep antibiotics, glutamine, 25 mM HEPES to which is added 3H-myo-inositol NEN #NET114A 1 mCi/mL, 25 Ci/mmol diluted 1:150 in loading media with a final specific radioactivity of 1 μCi/150 μL). Alternatively, the human and mouse albumin can be added after the overnight labeling step before the addition of LiCl.

The assay is typically run the next day after 18 h labeling. On the day of the assay, 5 μL of 300 mM LiCl is added to all wells and incubated at 37 degrees for 20 min. 0.75 μL of 200× compounds are added and incubated with the cells for 60 min at 37 degrees. The media is then aspirated off and the assay terminated with the addition of 60 μL 10 mM formic acid. The cells are lysed for 60 min at room temperature. 15-30 μL of lysate is mixed with 70 μL/1 mg YSi SPA beads (Amersham) in clear bottom Isoplates. The plates are shaken for 2 h at room temperature. Beads are allowed to settle and the plates are counted in the Wallac Microbeta.

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

The following Examples are provided to illustrate the invention and are not to be construed as limiting the invention in any manner. The scope of the invention is defined by the appended claims.

Methods of Synthesis of the Compounds of the Present Invention:

The compounds of the present invention can be prepared according to the procedures of the following Examples, using appropriate materials. The compounds illustrated in the examples are not, however, to be construed as forming the only genus that is considered as the invention. The Examples further illustrate details for the preparation of the compounds of the present invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

LIST OF ABBREVIATIONS

| Alk | = | alkyl |
|---|---|---|
| APCI | = | atmospheric pressure chemical ionization |
| Ar | = | aryl |
| Boc | = | tert-butoxycarbonyl |
| br | = | broad |
| Cbz | = | benzyloxycarbonyl |
| $CH_2Cl_2$ | = | dichloromethane |
| d | = | doublet |
| DIPEA | = | N,N-diisopropylethylamine |
| DMAP | = | 4-dimethylaminopyridine |
| DMF | = | N,N-dimethylformamide |
| DMSO | = | dimethylsulfoxide |
| ESI | = | electrospray ionization |
| EtOAc | = | ethyl acetate |
| h | = | hour(s) |
| HOAc | = | acetic acid |
| KOH | = | potassium hydroxide |
| LC-MS | = | liquid chromatography-mass spectroscopy |
| LiOH | = | lithium hydroxide |
| m | = | multiplet |
| min | = | minutes |
| MeOH | = | methyl alcohol |
| $MgSO_4$ | = | magnesium sulfate |
| MS | = | mass spectroscopy |
| NaOH | = | sodium hydroxide |
| $Na_2SO_4$ | = | sodium sulfate |
| $NH_4OAc$ | = | ammonium acetate |
| NMR | = | nuclear magnetic resonance spectroscopy |
| PE | = | petroleum ether |
| PG | = | protecting group |
| rt | = | room temperature |
| s | = | singlet |
| t | = | triplet |
| THF | = | tetrahydrofuran |
| TFA | = | trifluoroacetic acid |
| TLC | = | thin-layer chromatography |
| TsOH | = | p-toluenesulfonic acid |

INTERMEDIATE 1

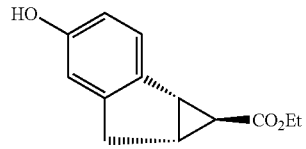

Ethyl (1S,1aS,6aR)-4-hydroxy-1,1a,6,6a-tetrahydrocyclopropa[a]indene-1-carboxylate Step A: 5-Hydroxyindan-1-one

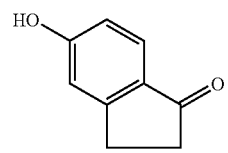

To a mixture of 5-methoxyindan-1-one (200 g, 1.235 mol) in 2 L of anhydrous dichloromethane was added $BBr_3$ (234 mL, 2.469 mol) slowly at −78° C. The mixture was warmed slowly to rt and stirred overnight. Then the mixture was poured slowly into ice-water (2 L) with vigorously stirring for 30 min. The result mixture was filtered to give a solid. The filtrate was separated, and the aqueous phase was extracted with EtOAc (2×500 mL). The combined organic phases were washed with brine (1 L) and dried over Na$_2$SO$_4$ and concentrated to dryness to obtain another batch of solid. The combined solids were dried in vacuo to give the title compound. $^1$H-NMR (400 MHz, MeOD): δ 7.55 (d, J=8.1 Hz, 1H), 6.78-6.84 (m, 2H), 3.03-3.06 (m, 2H), 2.60-2.63 (m, 2H) ppm.

Step B: 1-Oxo-2,3-dihydro-1H-inden-5-yl benzoate

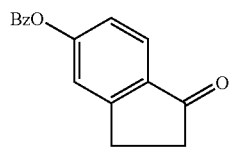

Benzoyl chloride (126.9 g, 0.900 mol) was added slowly to a stirred mixture of the product of Step A (121 g, 0.818 mol), triethylamine (99.1 g, 0.982 mol) and catalytic amount of DMAP (1 g, 8.18 mmol) in dichloromethane (1 L) at rt under nitrogen. The mixture was stirred overnight and diluted with dichloromethane (1 L). Then the solution was washed with water, hydrochloric acid (0.5 M, 2×1 L), and brine. The organic layer was dried over MgSO$_4$, filtered and the solvent was evaporated under reduced pressure. The residue was dried in vacuo to give the compound. $^1$H-NMR (400 MHz, CDCl$_3$): δ 8.19-8.22 (m, 2H), 7.83 (d, J=8.1 Hz, 1H), 7.65-7.69 (m, 1H), 7.52-7.55 (m, 2H), 7.37 (s, 1H), 7.22 (dd, J=8.1 Hz, J=2.0 Hz, 1H), 3.17-3.20 (m, 2H), 2.73-2.76 (m, 2H) ppm.

Step C: 1-Hydroxy-2,3-dihydro-1H-inden-5-yl benzoate

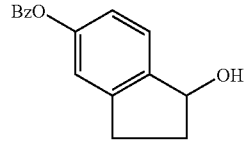

BH$_3$.THF (1 M solution in THF, 773.8 mL, 773.8 mmol) was added dropwise to a stirred mixture of the product of Step B (195 g, 773.8 mmol) in anhydrous THF at 0° C. under nitrogen, and the reaction mixture was stirred at rt overnight. The mixture was cooled to 0° C. and carefully quenched with methanol (500 mL). Cooling bath was removed, and the solution was stirred until bubbling stopped. The solvent was evaporated under reduce pressure. The residue was purified by column chromatography on silica gel (EtOAc:PE=1:10) to give the title compound. $^1$H-NMR (400 MHz, CDCl$_3$): δ 8.19-8.22 (m, 2H), 7.62-7.66 (m, 1H), 7.52 (t, J=7.6 Hz, 2H), 7.45 (d, J=8.1 Hz, 1H), 7.06-7.10 (m, 2H), 5.25 (t, J=6.1 Hz, 1H), 3.05-3.12 (m, 1H), 2.81-2.89 (m, 1H), 2.49-2.58 (m, 1H), 1.96-2.04 (m, 2H) ppm.

Step D: 1H-Inden-6-yl benzoate

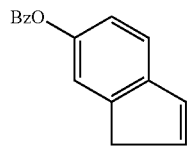

TsOH (850 mg, 9.449 mmol) was added to a stirred mixture of 1-hydroxy-2,3-dihydro-1H-inden-5-yl benzoate (120 g, 472.441 mmol) and MgSO$_4$ (113.4 g, 944.882 mmol) in toluene at rt under nitrogen, and the reaction mixture was stirred at 90-100° C. overnight. The solid was filtered off and the filtrate was concentrated under reduced pressure. The residue was purified by column chromatography (PE) to give the title compound. $^1$H-NMR (400 MHz, CDCl$_3$): δ 8.22-8.24 (m, 2H), 7.62-7.66 (m, 1H), 7.50-7.54 (m, 2H), 7.42 (d, J=8.1 Hz, 1H), 7.34 (d, J=1.2 Hz, 1H), 7.12 (dd, J=8.1 Hz, J=2.0 Hz, 1H), 6.88-6.90 (m, 1H), 6.57-6.59 (m, 1H), 3.44 (s, 2H) ppm.

Step E: Ethyl (1S,1aS,6aR)-4-(benzoyloxy)-1,1a,6,6a-tetrahydrocyclopropa[a]indene-1-carboxylate

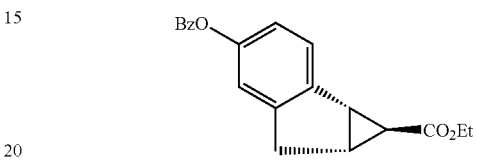

(+)-2,2'-Isopropylidenebis[(4R)-4-phenyl-2-oxazoline (849 mg, 2.542 mmol) was added to a stirring solution of 1H-inden-6-yl benzoate from Step D (30 g, 127.119 mmol) and Cu(I) triflate (657 mg, 1.271 mmol) in dichloromethane (300 mL) at rt under nitrogen. The solution was stirred at rt for 4 h. A solution of ethyl diazoacetate (29 g, 254.237 mmol) in dichloromethane (100 mL) was added at it through a syringe pump over a period of 72 h. Solvent was removed under reduce pressure, and the residue was purified by column chromatography on silica gel (PE) to give the title compound (about 50% enantiomeric excess). $^1$H-NMR (400 MHz, CDCl$_3$): δ 8.18 (d, J=7.1 Hz, 2H), 7.63 (t, J=7.6 Hz, 1H), 7.51 (t, J=7.1 Hz, 2H), 7.37 (d, J=8.1 Hz, 1H), 6.96-7.02 (m, 2H), 4.16 (q, J=7.1 Hz, 2H), 3.29-3.35 (m, 1H), 2.95-3.10 (m, 2H), 2.46-2.50 (m, 1H), 1.26-1.33 (m, 4H) ppm. MS: m/z 323.2 (M+1)$^+$.

Step F: Ethyl (1S,1aS,6aR)-4-hydroxy-1,1a,6,6a-tetrahydrocyclopropa[a]indene-1-carboxylate

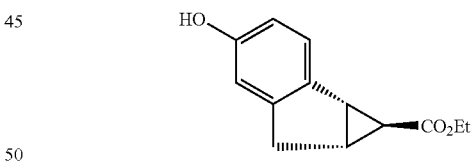

The benzoyl ester from Step E (30 g, 93.168 mmol) was dissolved in anhydrous ethanol (300 mL) and cooled to 0° C. under nitrogen. A solution of EtONa in EtOH (46.6 mL, 93.200 mmol) was slowly added. The resulting solution was stirred at room temperature for 4 hr. Most of the solvent was removed and the residue was carefully partitioned between ethyl acetate (200 mL) and HCl (aq, 0.5 M, 300 mL) and extracted with ethyl acetate (200 mL). The combined organic solution was washed with brine (200 mL), dried with sodium sulfate, and evaporated. The crude product was purified on silica gel column (EtOAc/PE=1:20) and then chiral prep-HPLC to obtain the pure title compound (enantiomeric excess: >95%). $^1$H-NMR (400 MHz, CDCl$_3$) δ 7.16 (d, J=8.4 Hz, 1H), 6.60-6.65 (m, 2H), 4.14 (q, J=7.2 Hz, 2H), 3.19-3.25 (m, 1H), 2.87-2.99 (m, 2H), 2.39-2.43 (m, 1H), 1.26 (t, J=7.2 Hz, 3H), 1.17-1.19 (m, 1H) ppm. MS: m/e 219.0 (M+1)$^+$.

Example 1

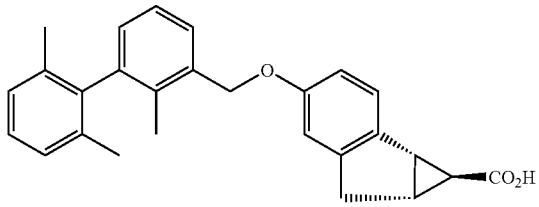 [SMILES: Cc1cccc(C)c1-c1cccc(COc2ccc3c(c2)C[C@H]2[C@H](C(=O)O)[C@@H]32)c1C]

(1S,1aS,6aR)-4-[(2,2',6'-Trimethylbiphenyl-3-yl)
methoxy]-1,1a,6,6a-tetrahydrocyclopropa[a] indene-
1-carboxylic acid Step A: Methyl 3-bromo-2-methylbenzoate

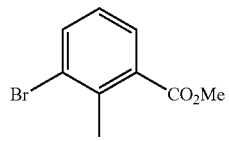

Trimethylsilyldiazomethane solution (2M in Hexane) (60.5 mL, 121 mmol) was added dropwise to a stirred solution of 3-bromo-2-methylbenzoic acid (26 g, 121 mmol) in benzene containing 20% of methanol (total: 300 mL) at rt until solution retained a yellow color. The mixture was concentrated to remove the organic solvent. The remaining oil was poured over a silica gel plug in a 60-mL filter frit funnel and eluting with 500 mL of hexane containing 10% ethyl acetate. The filtrate was then concentrated to dryness to afford the title compound as a bright yellow oil.

Step B: Methyl 2,2',6'-Trimethylbiphenyl-3-carboxylate

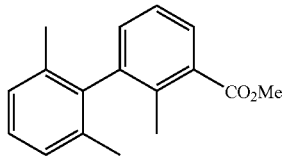 [SMILES: COC(=O)c1cccc(-c2c(C)cccc2C)c1C]

To a two-neck round bottom flask with a magnetic stirring bar, was added tris(dibenzylideneacetone)dipalladium(0) (120 mg, 0.131 mmol), tri-t-butylphosphonium tetrafluoroborate (76 mg, 0.262 mmol), cesium fluoride (2.65 g, 17.5 mmol), 2,6-dimethylphenylboronic acid (1.3 g, 8.73 mmol), and the compound from Step A (1 g, 4.4 mmol). One neck of the flask was connected to a vacuum line while another neck was fitted with a argon balloon. The flask was then purged 8-10 times with argon. The vacuum line was replaced with a septum and anhydrous THF (10 mL) was added by syringe. The mixture was stirred in a 70° C. oil bath for 16 h. The reaction solution was filtrated and concentrated. The residue was purified by column chromatography on silica gel Biotage 40S™, eluting with EtOAc/hexane (10:1) to give the title compound as a clear oil.

Step C: (2,2',6'-Trimethylbiphenyl-3-yl)methanol

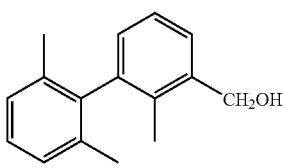 [SMILES: Cc1cccc(C)c1-c1cccc(CO)c1C]

To a solution of the product from Step B (1 g, 3.93 mmol) in diethyl ether (20 ml) was carefully added lithium aluminum hydride (1.5 g, 3.93 mmol). The mixture was stirred at room temperature for 16 h. Saturated aqueous ammonium chloride solution was added dropwise until no hydrogen gas was being generated. A few more drops of saturated aqueous ammonium chloride solution was added and the mixture was stirred at room temperature for 30 min and filtered. The filtrate was dried on magnesium sulfate and concentrated to dryness to give the title compound as a colorless oil.

Step D: (2,2',6'-Trimethylbiphenyl-3-yl)methyl methanesulfonate

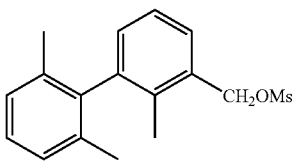

To a solution of the product from Step C (1 g, 4.42 mmole) in dichloromethane (10 mL) was added triethylamine (0.54 g, 5.3 mmol) followed by methanesulfonyl chloride (0.6 g, 5.3 mmol) dropwise. The mixture was stirred at room temperature for 3-4 h. It was then washed with water and brine, and dried over magnesium sulfate, and concentrated to dryness to give the title compound as a colorless oil.

Step E: Ethyl (1S,1aS,6aR)-4-[(2,2',6'-trimethylbiphenyl-3-yl)methoxy]-1,1a,6,6a-tetrahydrocyclopropa[a]indene-1-carboxylate

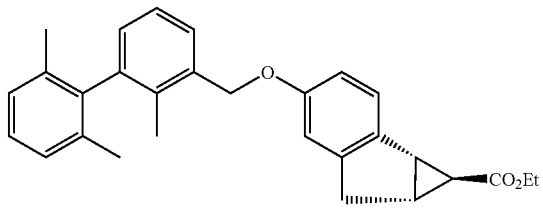 [SMILES: CCOC(=O)[C@H]1[C@@H]2Cc3cc(OCc4cccc(-c5c(C)cccc5C)c4C)ccc3[C@@H]21]

To a solution of the product from Step D (0.95 g, 3.12 mmol) and intermediate 1 (0.68 g, 3.12 mmol) in anhydrous DMF (5 mL), was added cesium carbonate (2.01 g, 6.24 mmol). The mixture was stirred at room temperature for 16 h, then diluted with water (10 mL) and extracted with ethyl acetate (2×10 mL). The organic extracts were combined, washed with water (10 mL), dried with magnesium sulfate and concentrated. The residue was purified by column chromatography on silica gel Biotage 40S™, eluting with EtOAc/hexane (10:1) to give the title compound as a crystalline solid.

Step F: (1S,1aS,6aR)-4-[(2,2',6'-Trimethylbiphenyl-3-yl)methoxy]-1,1a,6,6a-tetrahydrocyclopropa[a]indene-1-carboxylic acid

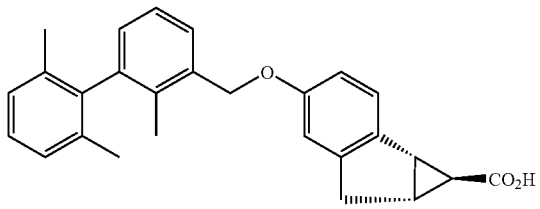 [SMILES: Cc1cccc(C)c1-c1cccc(COc2ccc3c(c2)C[C@H]2[C@H](C(=O)O)[C@@H]32)c1C]

Sodium hydroxide solution (0.69 ml, 10 N, 6.9 mmol) was added to a stirred solution of ester from Step E (0.98 g, 2.3 mmol) in THF (4 mL), methanol (4 mL), and water (2 mL) at rt under nitrogen. The mixture was stirred at 60° C. overnight. The solution was neutralized with conc. HCl (0.57 mL), concentrated to remove organic solvent. The residue was dissolved in ethanol/water (10 mL, 1:1) warmed to obtain a clear solution and then cooled in refrigerator to produce a precipitation. The solid was collected by filtration and dried in air to give the title compound as a white crystalline solid. $^1$H NMR (500 MHz, CDCl$_3$): δ 7.44 (1H, d, J=7.5 Hz), 7.29 (2H, m), 7.20 (1H, dd, J=6.5, 8.5 Hz), 7.15 (1H, s), 7.14 (1H, d, J=7.5 Hz), 7.05 (1H, d, J=7.5 Hz), 6.87 (1H, s), 6.85 (1H, dd, J=8.5, 2.0 Hz), 5.05 (2H, s), 3.31 (1H, dd, J=18, 6.5 Hz), 3.07 (1H, d, J=18 Hz), 3.00 (1H, d, J=6.5 Hz), 2.53 (1H, m), 1.99 (3H, s), 1.97 (6H, s), 1.25 (1H, t, J=2.5 Hz) ppm. MS: m/e 399 (M+1)$^+$.

Example 2

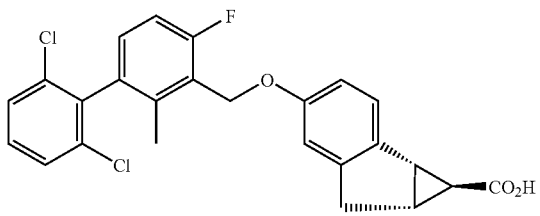 [SMILES: Cc1c(-c2c(Cl)cccc2Cl)ccc(F)c1COc1ccc2c(c1)C[C@H]1[C@H](C(=O)O)[C@@H]21]

(1S,1aS,6aR)-4-[(2',6'-dichloro-4-fluoro-2-methylbiphenyl-3-yl)methoxy]-1,1a,6,6a-tetrahydrocyclopropa[a]indene-1-carboxylic acid Step A: 6-Fluoro-3-iodo-2-methylbenzoic acid

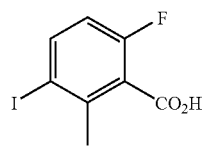

N-Iodosuccinimide (7.47 g, 33.2 mmol) was added dropwise to a stirred solution of 6-fluoro-2-methylbenzoic acid (5.12 g, 33.2 mmol) in trifluoromethanesulfonic acid (50 mL) at room temperature. The mixture was stirred at room temperature overnight, poured into ice/water and stirred for 3 h until solid produced. The precipitate was collected, washed with water, and air dried to give the title compound as a yellow solid.

Step B: Methyl 6-fluoro-3-iodo-2-methylbenzoate

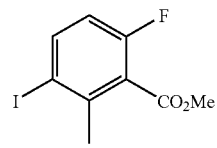

Trimethylsilyldiazomethane solution (2 M in Hexane) (18 mL, 35 mmol) was added dropwise to a stirred solution of the product of Step A (7.3 g, 33.2 mmol) in benzene containing 20% of methanol (total: 100 mL) at room temperature until solution retained a yellow color. The mixture was concentrated to remove the organic solvent. The remaining oil was poured over a silica gel plug in a 60-mL filter frit funnel and eluting with 200 mL of hexane containing 10% ethyl acetate. The filtrate was then concentrated to dryness to give the title compound as a bright yellow oil.

Step C: (6-Fluoro-3-iodo-2-methylphenyl)methanol

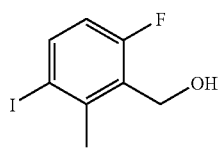

To a solution of the product from Step B (5.5 g, 18.7 mmol) in diethyl ether (20 ml) was carefully added lithium aluminum hydride (0.8 g, 18.7 mmol). The mixture was stirred at room temperature for 16 h. Saturated aqueous ammonium chloride solution was added dropwise until no hydrogen gas was being generated. A few more drops of saturated aqueous ammonium chloride solution were added and the mixture was stirred at room temperature for 30 min and filtered. The filtrated was dried over magnesium sulfate and concentrated to dryness to give the title compound as a colorless oil.

Step D: 2-(Chloromethyl)-1-fluoro-4-iodo-3-methylbenzene

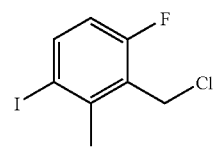

To a solution of the product of Step C (4.01 g, 15.4 mmol) in anhydrous benzene (40 mL) was added dropwise thionyl chloride (3.7 g, 30.8 mmol). The mixture was stirred 80° C. overnight. The mixture was cooled to rt, washed with saturated aqueous sodium bicarbonate solution, water and brine, and dried over magnesium sulfate, and concentrated to dryness to give the title compound as a colorless oil.

Step E: Ethyl (1S,1aS,6aR)-4-[(6-fluoro-3-iodo-2-methylbenzyl)oxy]-1,1a,6,6a-tetrahydrocyclopropa[a]indene-1-carboxylate

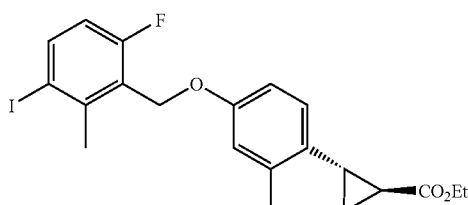

To a solution of the product of Step D (3.7 g, 13.0 mmol) and intermediate 1 (2.84 g, 13.0 mmol) in anhydrous DMF (20 ml), was added cesium carbonate (8.5 g, 26.0 mmol). The mixture was stirred at rt for 16 h, then diluted with water (30 mL) and extracted with ethyl acetate (2×10 mL). The organic extracts were combined, washed with water (10 mL), dried with magnesium sulfate and concentrated. The residue was purified by column chromatography on silica gel Biotage 40S™, eluting with EtOAc/hexane (10:1) to give the title compound as a crystalline solid.

Step F: Ethyl (1S,1aS,6aR)-4-[(2',6'-dichloro-4-fluoro-2-methylbiphenyl-3-yl)methoxy]-1,1a,6,6a-tetrahydrocyclopropa[a]indene-1-carboxylate

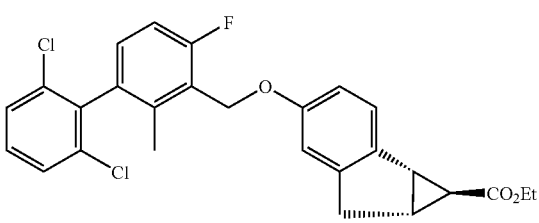 [SMILES: CCOC(=O)[C@H]1[C@@H]2Cc3cc(OCc4c(F)ccc(-c5c(Cl)cccc5Cl)c4C)ccc3[C@@H]21]

To a two-neck round bottom flask with a magnetic stirring bar, was added tris(dibenzylideneacetone)dipalladium(0) (29.5 mg, 0.032 mmol), tri-t-butylphosphonium tetrafluoroborate (18.6 mg, 0.064 mmol), cesium fluoride (652 g, 4.29 mmol), 2,6-dichlorophenylboronic acid (409 mg, 2.15 mmol), and the product of Step E (500 mg, 1.07 mmol). One neck of the flask was connected to a vacuum line while another neck was fitted with an argon balloon. The flask was then purged 8-10 times with argon. The vacuum line was replaced with a septum and anhydrous THF (10 mL) was added by syringe. The mixture was stirred in a 70° C. oil bath for 16 h. The reaction solution was filtrated and concentrated. The residue was carried on to hydrolysis at the next step without purification.

Step G: (1S,1aS,6aR)-4-[(2',6'-dichloro-4-fluoro-2-methylbiphenyl-3-yl)methoxy]-1,1a,6,6a-tetrahydrocyclopropa[a]indene-1-carboxylic acid

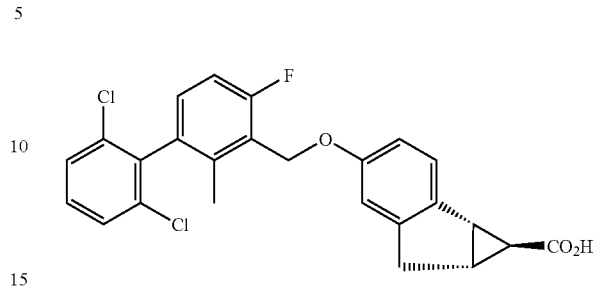

Sodium hydroxide solution (0.69 mL, 10 N, 6.9 mmol) was added to a stirred solution of the above mixture in THF (2 mL), methanol (2 mL), and water (1 mL) at rt under nitrogen. The mixture was stirred at 60° C. overnight. The solution was neutralized with conc. HCl (0.57 mL) and concentrated to remove organic solvent. The residue was dissolved in acetonitrile and water and purified by preparative HPLC. Fractions containing the product were combined and freeze-dried to afford the title compound as a white crystalline solid. $^1$H NMR (500 MHz, CDCl$_3$): δ 7.44 (2H, d, J=8.0 Hz), 7.29 (2H, m), 7.10 (2H, m), 6.88 (1H, s), 6.85 (1H, d, J=8.5 Hz), 5.14 (2H, s), 3.31 (1H, dd, J=18, 6.5 Hz), 3.07 (1H, d, J=18 Hz), 3.00 (1H, d, J=6.5 Hz), 2.53 (1H, m), 2.11 (3H, s), 1.29 (1H, brs) ppm. MS: m/e 457 (M+1)$^+$.

The following Examples in Table 1 were made by essentially following the same procedures described for Examples 1-3.

TABLE 1

| Example | X | MS (M + 1) |
|---|---|---|
| 3 | (3-methyloxetan-3-yl)methoxy-2,6-dimethylbiphenyl-3-yl | 467.3 (M + 1-H$_2$O) |
| 4 | (3-methyloxetan-3-yl)methoxy-2',6-dimethylbiphenyl-3-yl variant | 482.7 (M + 1-H$_2$O) |

TABLE 1-continued

| Example | X | MS (M + 1) |
|---|---|---|
| 5 | | 485.6 (M + 1-H₂O) |
| 6 | | 433.3 |
| 7 | | 431.4 (M + 1-H₂O) |
| 8 | | 429.3 |
| 9 | | 509.1 |
| 10 | | 547.1 |

EXAMPLE OF A PHARMACEUTICAL COMPOSITION

As a specific embodiment of an oral pharmaceutical composition, a 100 mg potency tablet is composed of 100 mg of any one of Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound which is selected from the group consisting of:

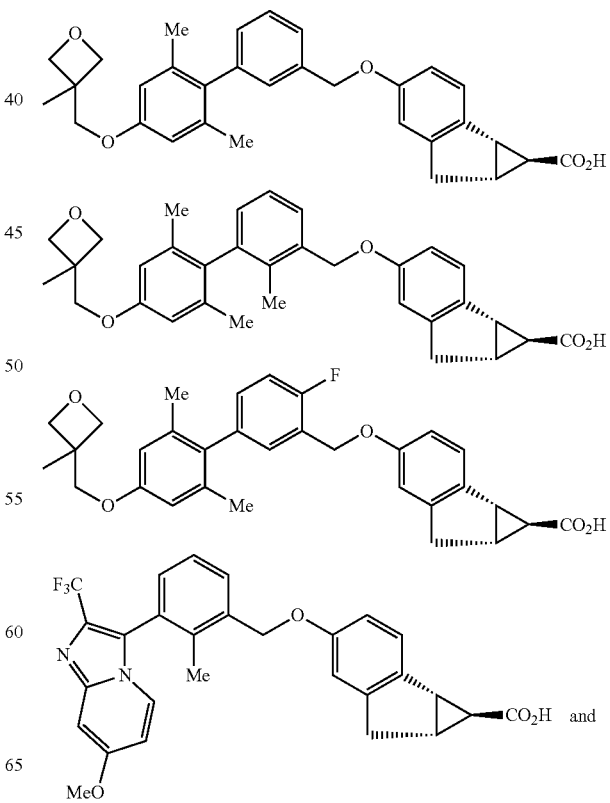

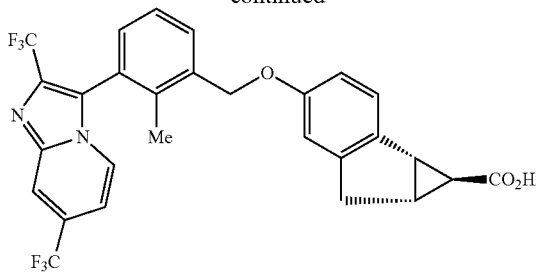

or a pharmaceutically acceptable salt thereof.

2. A pharmaceutical composition comprising a compound of claim 1, or a pharmaceutically acceptable salt thereof, and a pharmaceutically acceptable carrier.

3. A method of treating type 2 diabetes mellitus in a patient in need of treatment comprising the administration to the patient of a therapeutically effective amount of compound of claim 1, or a pharmaceutically acceptable salt thereof.

4. A pharmaceutical composition comprising
(1) a compound of claim 1 or a pharmaceutically acceptable salt thereof;
(2) one or more compounds selected from the group consisting of:
  (a) PPAR gamma agonists and partial agonists;
  (b) biguanides;
  (c) protein tyrosine phosphatase-1B (PTP-1B) inhibitors;
  (d) dipeptidyl peptidase IV (DP-IV) inhibitors;
  (e) insulin or an insulin mimetic;
  (f) sulfonylureas;
  (g) α-glucosidase inhibitors;
  (h) agents which improve a patient's lipid profile, said agents being selected from the group consisting of (i) HMG-CoA reductase inhibitors, (ii) bile acid sequestrants, (iii) nicotinyl alcohol, nicotinic acid or a salt thereof, (iv) PPARα agonists, (v) cholesterol absorption inhibitors, (vi) acyl CoA:cholesterol acyltransferase (ACAT) inhibitors, (vii) CETP inhibitors, and (vii) phenolic anti-oxidants;
  (i) PPARα/γ dual agonists,
  (j) PPARδ agonists,
  (k) antiobesity compounds,
  (l) ileal bile acid transporter inhibitors;
  (m) anti-inflammatory agents;
  (n) glucagon receptor antagonists;
  (o) GLP-1;
  (p) GIP-1;
  (q) GLP-1 analogs; and
  (r) HSD-1 inhibitors; and
(3) a pharmaceutically acceptable carrier.

* * * * *